US00RE34751E

United States Patent [19]

Thompson

[11] E Patent Number: Re. 34,751

[45] Reissued Date of Patent: Oct. 4, 1994

[54] COSMETIC PRODUCT

[75] Inventor: Harold R. Thompson, Norwell, Mass.

[73] Assignee: The Gillette Company, Boston, Mass.

[21] Appl. No.: 819,824

[22] Filed: Jan. 13, 1992

Related U.S. Patent Documents

Reissue of:

[64] Patent No.: 5,007,755
Issued: Apr. 16, 1991
Appl. No.: 417,260
Filed: Oct. 5, 1989

[51] Int. Cl.[5] ..... A45D 40/06; A45D 40/08

[52] U.S. Cl. ..... 401/175; 401/171; 401/176; 401/266

[58] Field of Search ..... 401/175, 266, 171, 172, 401/174, 176

[56] References Cited

U.S. PATENT DOCUMENTS

| | | | |
|---|---|---|---|
| 718,969 | 1/1903 | Altshul | 401/176 |
| 1,988,088 | 1/1935 | Philippe . | |
| 1,994,890 | 3/1935 | Kallenbach . | |
| 2,085,446 | 6/1937 | Philippe . | |
| 2,379,105 | 6/1945 | Rosa . | |
| 2,917,765 | 12/1959 | Jakubowski . | |
| 3,226,762 | 1/1966 | Norman . | |
| 4,664,547 | 5/1987 | Rosenwinkel | 401/175 |

FOREIGN PATENT DOCUMENTS

| | | | |
|---|---|---|---|
| 0312165 | 4/1989 | European Pat. Off. . | |
| 645184 | 6/1928 | France | 401/175 |
| 892804 | 1/1944 | France | 401/176 |
| 481726 | 6/1953 | Italy | 401/175 |

*Primary Examiner*—Steven A. Bratlie
*Attorney, Agent, or Firm*—Fish & Richardson

[57] ABSTRACT

A package cosmetic product includes container structure that has application surface structure at one end, dispensing structure at the opposite end that is movable towards the application surface structure, and gelled cosmetic material disposed in the container between the dispensing structure and the application surface structure. The application surface structure has an application surface with an array of dispensing ports, each port being at the end of and in direct communication with an elongated distribution passage. The array of distribution passages is defined by an interconnected array of elongated divider webs shaped to provide each distribution passage with a flared entrance port and a relieved dispensing port region at the application surface. Movement of the dispensing structure towards the application surface structure extrudes the gelled cosmetic material through the array of elongated distribution passages to present a metered quantity of the gelled cosmetic material at the application surface for application to the skin surface to be treated.

36 Claims, 1 Drawing Sheet

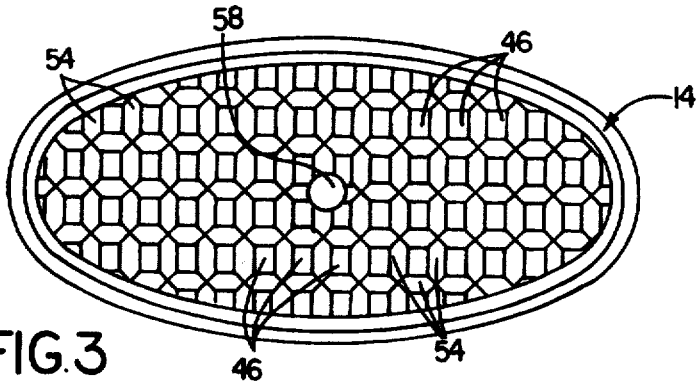
FIG.3
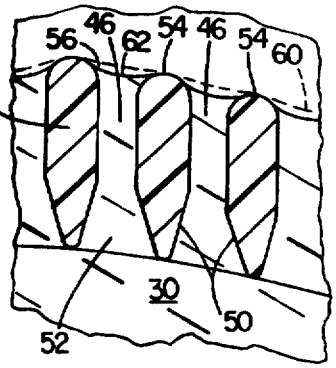
FIG.4
FIG.1
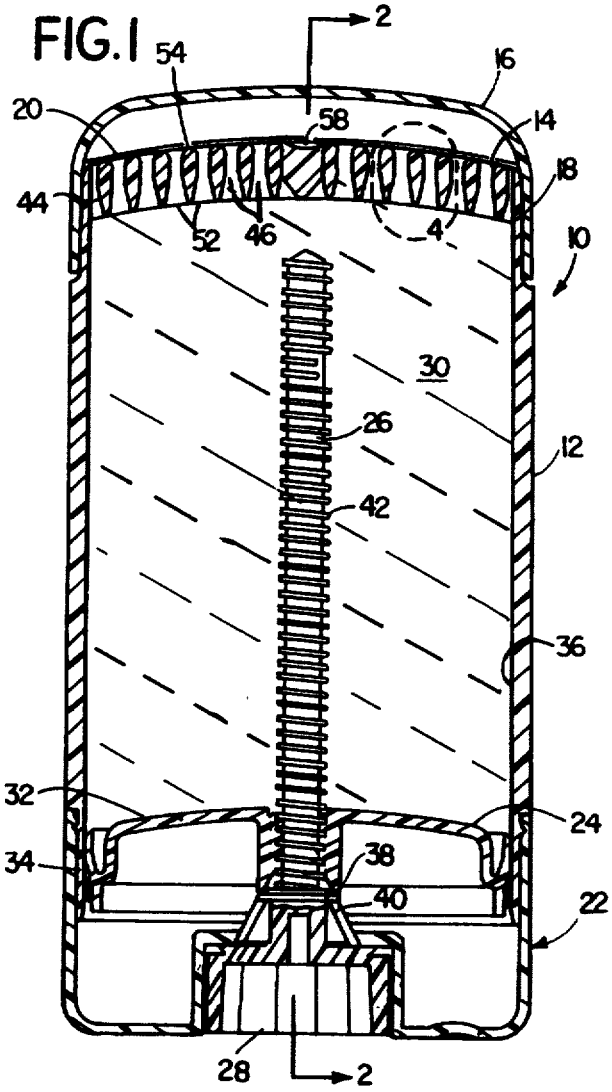
FIG.2
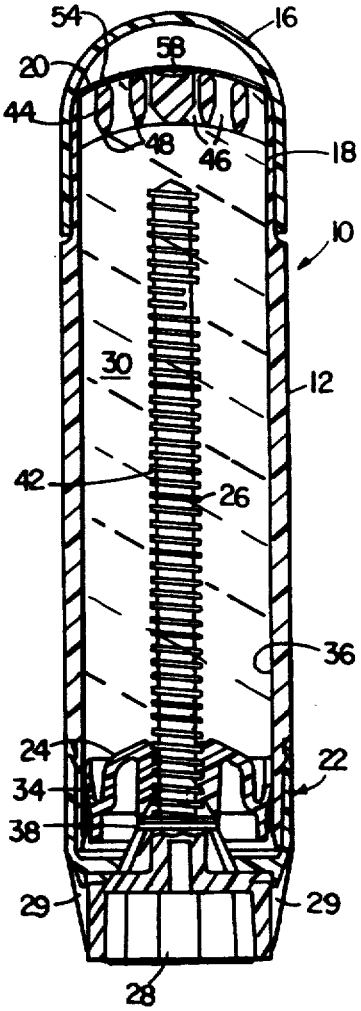

COSMETIC PRODUCT

Matter enclosed in heavy brackets [ ] appears in the original patent but forms no part of this reissue specification; matter printed in italics indicates the additions made by reissue.

This invention relates to cosmetic products, and more particularly to packaged cosmetic products.

Cosmetic products have a variety of viscosities. Liquid cosmetic products, for example, are commonly supplied in bottles and poured therefrom for application to the skin. Other solid form cosmetic products are applied by rubbing an exposed surface of the solid product on the skin. A third class of cosmetic products are gelled materials which have substantial physical stability but less stability than solid form products. Such gel materials have viscosities in the range of 50,000 to 200,000 centipoises, and preferably are packaged in a container for handling and retention of the product within the container when not in use and distributed dispensing from an application surface of the container for application to the body area to which it is desired to apply the cosmetic product but present difficulties such as oozing or leakage in storage and instability in dispensing.

In accordance with the invention, there is provided a packaged cosmetic product that includes gelled cosmetic material disposed within container structure that has application surface structure at one end and dispensing structure at the opposite end that is movable towards the application surface structure, the gelled cosmetic material being disposed in the container between the dispensing structure and the application surface structure. The application surface structure has an application surface with an array of dispensing ports, each port being at the end of and in direct communication with an elongated distribution passage. The array of distribution passages are defined by an interconnected array of elongated divider webs shaped to provide each distribution passage with a flared entrance port and a relieved dispensing port region at the application surface. Movement of the dispensing structure towards the application surface structure extrudes the gelled cosmetic material concurrently through the array of elongated distribution passages to present a metered quantity of the gelled cosmetic material at the application surface for application to the skin surface to be treated.

Preferably, the container structure has an annular wall of oval shape that is integral with the application surface structure and the application surface is convex and has a greater radius in the longitudinal direction than in the transverse direction. The dispensing ports may be of various shape, such as hexagonal, rectangular or circular; the divider webs typically have a length of at least four millimeters and a width of less than about two millimeters; the number of dispensing ports per square centimeter of application surface is in the range of one to seven, preferably about four to six; the minimum cross-sectional area of the distribution passages (at a point intermediate the entrance and dispensing ports) may range from five to forty square millimeters and preferably the passages have a length of at least about twice their width dimensions. In a particular embodiment, the minimum cross-sectional area of the distribution passages is about eight square millimeters; the passage of length is at least four millimeters, and in a particular embodiment is about seven millimeters with a tapered entrance length of about two millimeters, a four millimeter length of uniform (minimum) cross-sectional area, and a smoothly curved dispensing port region that merges smoothly with adjacent dispensing port regions. Preferably, the dispensing ports are disposed in a symmetrical array of at least fifteen ports and in a particular embodiment there are over fifty ports, each with an effective cross sectional area of about eight square millimeters in an application surface area of about twelve square centimeters.

The dispensing port array preferably is uniformly dispersed over the application surface and the distribution passage walls preferably have a thickness of less than two millimeters, and a uniform dispensing of the gelled cosmetic product (an antiperspirant in a particular embodiment) over the application surface area is provided. While the distribution passages in a particular embodiment are of equal length, in other embodiments the passages may be of different or graduated lengths as desired to provide differential distribution of the dispensed cosmetic product at the application surface. In a particular embodiment, the gel cosmetic material is a stable water in oil emulsion that includes an aqueous phase that includes water and an antiperspirant active ingredient; an oil phase that includes a volatile silicone; and a minor amount of another cosmetic ingredient. Preferably, the aqueous phase is at least about 70% by weight of the emulsion and the antiperspirant active ingredient is selected from the group consisting of aluminum zirconium chlorohydrate and aluminum chlorohydrate.

Other features and advantages will be seen as the following description of a particular embodiment progresses, in conjunction with the drawings in which:

FIG. 1 is a sectional elevation view of a packaged gel antiperspirant product in accordance with the invention;

FIG. 2 is a sectional view taken along the line 2—2 of FIG. 1;

FIG. 3 is a top plan view of the antiperspirant product shown in FIG. 1 (with the cover and protective sheet removed) showing aspects of the application surface structure; and FIG. 4 is an enlarged view taken along the line 4—4 of a portion of the application surface and distribution passage structures.

DESCRIPTION OF PARTICULAR EMBODIMENT

The packaged cosmetic product 10 shown in FIG. 1 includes annular container body 12 of optically clear polymeric material such as polyethylene terephthalate (PET) that has a width of about five centimeters, a depth of about 2.5 centimeters, a height of about eight centimeters, a wall thickness of about two millimeters, and is of oval cross-sectional shape as indicated in FIG. 3. Formed at the top of body 12 and integral therewith is apertured application surface 14 of compound convexity over which removable cover 16 is frictionally secured by engagement with wall portion 18. A removable seal strip 20 is disposed over application surface 14 for storage and shipping and is removed prior to product use. Base 22 is snap fitted to the lower end of body 12.

Disposed within the chamber formed by container body 12 is a dispensing mechanism that includes platform member 24, threaded shaft 26 and actuator 28 exposed by apertures 29 on opposite sides of base 22 for manual engagement and dispensing the gel antiperspirant product 30 through the apertured application surface 14. Platform member 24 has convex surface 32 and circumferential wiping rib 34 in wiping engagement with inner surface 36 of body 12. Threadedly secured to platform 24 is drive shaft 26 that has integral actuator knob 28 at its base, annular latch flange 38 that is held by securing flanges 40 of base 20 and modified single lead Acme thread 42 (six threads per centimeter) that has a thread length of about seven centimeters, an outer diameter of about 0.6 centimeter and a thread depth of about two millimeters. Disposed in container body 12 above platform 24 and application surface 14 is an optically clear antiperspirant product 30 that has a viscosity of about 100,000 centipoises at 22° C. (all references to centipoise viscosity values herein being at 22° C.). Product 30 is a stable water-in oil emulsion that includes an aqueous phase (about 75% by weight of the emulsion) that includes water, propylene glycol and an antiperspirant active ingredient such as aluminum zirconium chlorohydrate or aluminum chlorohydrate; an oil phase that includes a volatile silicone and a polyether substituted silicone emulsifier of cyclomethicone and dimethicone copolyol; ethanol as an adjunct; and minor amounts of other cosmetic ingredients such as fragrances and preservatives.

Applicator surface structure 44 that is integral with body 12 and includes application surface 14 and an array of distribution passages 46 defined by an array of elongated interlocking divider webs 48 that have inclined lower (leading) end portions 50 to define flared entrance ports 52 and curved upper (trailing) end portions 54 to define relieved dispensing ports 56 at application surface 14. Each passage 46, as indicated in FIG. 3, is of rectangular configuration and about three millimeters wide and about two millimeters deep at its minimum cross sectional area. The tapered walls 50 define an entrance port 52 of about four millimeters length and about three millimeters width, the web body has a maximum width of about one and one half millimeters and the dispensing end surface 54 is smoothly curved at a radius of about 0.8 millimeter. The length of the divider webs 48 is about 0.6 centimeter with the tapered entrance portion 50 having a length of about two millimeters. The enlarged area 58 at the center of application surface 14 provides a gate for molding, and may be proportioned and located as appropriate in particular applications.

The pitch of dispenser screw thread 42 is selected in proportion with the diameter of actuator knob 28 and the size of the openings 29 in base 22 so that one or two advancing actions of the actuator knob 28 (to produce a shaft rotation of about 100°) advances the antiperspirant product 30 about half a millimeter through the distribution passages 46 to place the surface 60 of the gel cosmetic material 30 substantially at the application surface 14. Rubbing the application surface 14 against the skin with modest normal pressure transfers the gel antiperspirant material 30 to the skin in a metered dispensing action portion so that the exposed gel antiperspirant material has a surface 62 of curved recessed configuration as indicated in FIG. 4. After application, cap 16 is replaced on container 12 for protective storage until the next product application is desired.

The package provides convenient and effective dispensing of the gel cosmetic product in a controlled manner and stable manner.

While a particular embodiment of the invention has been shown and described, various modifications will be apparent to those skilled in the art, and therefore it is not intended that the invention be limited to the disclosed embodiment or to details thereof, and departures may be made therefrom within the spirit and scope of the invention:

What is claimed is:

1. A packaged cosmetic product comprising container structure that includes annular chamber wall structure, application surface structure at one end of said annular chamber wall structure, said application surface structure defining an application surface with an array of dispensing ports and having an array of elongated divider webs that define a corresponding array of directly connected distribution passages, said elongated divider webs having body portions, leading end surface portions of width less than said distribution passages to define flared entrance ports to said distribution passages, and relieved trailing end portions to define dispensing ports of cross-sectional areas greater than the minimum cross-sectional areas of the corresponding distribution passages at said application surface, gel cosmetic material of less than 200,000 centipoises viscosity in said container structure, and dispenser structure for urging said gel cosmetic material through said distribution passages and said corresponding directly connected dispensing ports to said application surface.

2. The product of claim 1 wherein said distribution passages are of equal length.

3. The product of claim 1 wherein said chamber wall structure is of oval configuration and said application surface is convex and has a greater radius in the longitudinal direction than in the transverse direction.

4. The product of claim 1 wherein each said web body portion has a width of less than about two millimeters.

5. The product of claim 1 wherein the number of said dispensing ports per square centimeter in said application surface is in the range of one to seven.

6. The product of claim 1 wherein there are at least four of said dispensing ports per square centimeter in said application surface.

7. The product of claim 1 wherein the minimum cross-sectional area of each said distribution passage is in the range of from five to forty square millimeters.

8. The product of claim 1 wherein the length of each said distribution passage is at least about four millimeters.

9. The product of claim 1 wherein each said web has a smoothly curved leading end surface, and each said distribution passage has a tapered entrance portion, an intermediate length of uniform cross-sectional area, and a smoothly curved dispensing port region that merges smoothly with adjacent dispensing port regions at said application surface.

10. The product of claim 1 wherein said dispensing ports are disposed at said application surface in a symmetrical array of at least fifteen ports, each said dispensing port having an effective cross-sectional area of about eight square millimeters in an application surface area of about twelve square centimeters.

11. The product of claim 1 wherein said dispensing ports are of polygonal configuration and are uniformly dispersed over said application surface.

12. The product of claim 11 wherein said chamber wall structure is of oval configuration, said application surface is convex and has a greater radius in the longitudinal direction than in the transverse direction, each said web has a smoothly curved leading end surface, each said distribution passage has a tapered entrance portion, an intermediate length of uniform cross-sectional area; and a smoothly curved dispensing port region that merges smoothly with adjacent dispensing portion regions at said application surface and each said distribution passages web portion has a thickness of less than two millimeters.

13. The product of claim 12 wherein said application surface structure is integral with said annular wall of said container, the density of said passages in said application surface structure is in the order of one to seven per square centimeter, the minimum cross-sectional area of each said passage is in the range of five to forty square millimeters, said passages are distributed uniformly through the application surface structure, said passages have a length of at least about one half centimeter and each said passage has a width dimension of less than one-half the passage length dimension, and each said divider web body portion is less than two millimeter in thickness.

14. The product of claim 13 wherein said distribution passages are of equal length[, and each said web has a width of less than about two millimeters].

15. The product of claim 13 wherein said gel cosmetic material is a stable water-in-oil emulsion that includes an aqueous phase that includes water and an antiperspirant active ingredient; an oil phase that includes a volatile silicone; and a minor amount of another cosmetic ingredient.

16. The product of claim 15 wherein said aqueous phase is at least about 70% by weight of the emulsion and said antiperspirant active ingredient is selected from the group consisting of aluminum zirconium chlorohydrate and aluminum chlorohydrate.

17. The product of claim 1 wherein said gel cosmetic material has a viscosity in the range of 50,000 to 150,000 centipoises.

18. The product of claim 17 wherein said gel cosmetic material includes an active antiperspirant ingredient.

19. The product of claim 17 wherein said chamber wall structure is of oval configuration, said application surface is convex and has a greater radius in the longitudinal direction than in the transverse direction, each said web has a smoothly curved leading end surface, each said distribution passage has a tapered entrance portion, an intermediate length of uniform cross-sectional area, and a smoothly curved dispensing port region that merges smoothly with adjacent dispensing portion regions at said application surface, and each said distribution passage web body portion has a thickness of less than two millimeters.

20. A packaged antiperspirant product comprising container structure that includes annular chamber wall structure, application surface structure at one end of said annular chamber wall structure integral with said annular wall of said container, gel cosmetic material of less than 200,000 centipoises viscosity in said container structure, said gel cosmetic material being a stable emulsion that includes an antiperspirant active ingredient, said application surface structure defining an application surface with an array of dispensing ports and having an array of elongated divider webs that define a corresponding array of directly connected distribution passages, said elongated divider webs having smoothly curved entrance end surfaces and tapered leading end portions to define flared entrance ports to said distribution passages, and smoothly curved trailing end surfaces that define dispensing ports at said application surface of cross-sectional areas greater than the minimum cross-sectional areas of the corresponding distribution passages, the radii of said curved entrance end surfaces being less than the radii of said curved trailing end surfaces, said dispensing ports being disposed at said application surface in a symmetrical array of at least fifteen ports, the density of said passages in said application surface structure being at least four per square centimeter, the minimum cross-sectional area of each said passage being in the range of five to forty square millimeters, said passages being distributed uniformly through the application surface structure and having a length of at least about one-half centimeter, each said passage having a width dimension of less than one half the passage length dimension, each said divider web being less than two millimeters in thickness, and dispenser structure for urging said cosmetic material through said distribution passages and said corresponding directly connected dispensing ports to said application surface.

21. The product of claim 20 wherein the radius of each said curved trailing end surface is about 0.8 millimeter.

*22. A packaged cosmetic product comprising*

*container structure that includes annular chamber wall structure,*

*application surface structure at one end of said annular chamber wall structure, said application surface structure defining an application surface with an array of dispensing ports and having an array of elongated divider webs that define a corresponding array of directly connected distribution passages, said elongated divider webs having body portions, leading end surface portions of width less than said distribution passages to define flared entrance ports to said distribution passages, and trailing end portions to define dispensing ports at said application surface of cross-sectional areas at least equal to the minimum cross-sectional areas of the corresponding distribution passages,*

*gel cosmetic material of less than 200,000 centipoises viscosity in said container structure, and*

*dispenser structure for urging said gel cosmetic material through said distribution passages and said corresponding directly connected dispensing ports to said application surface.*

*23. The product of claim 22 wherein said gel cosmetic material has a viscosity in the range of 50,000 to 150,000 centipoises.*

*24. The product of claim 23 wherein said dispensing ports are disposed at said application surface in a symmetrical array of at least fifteen ports, each said dispensing port having an effective cross-sectional area of about eight square millimeters in an application surface area of about twelve square centimeters.*

*25. The product of claim 23 wherein said dispensing ports are of polygonal configuration.*

*26. The product of claim 25 wherein each said dispensing port is of cross-sectional area greater than the minimum cross-sectional area of the corresponding distribution passage.*

*27. The product of claim 26 wherein said chamber wall structure is of oval configuration, said application surface is convex and has a greater radius in the longitudinal direction than in the transverse direction, each said web has a smoothly curved leading end surface, each said distribution passage has a tapered entrance portion, an intermediate length of uniform cross-sectional area, and a smoothly curved dispensing port region that merges smoothly with adjacent dispensing portion regions at said application surface, and each said distribution passage web portion has a thickness of less than two millimeters.*

*28. A dispenser for gel cosmetic product comprising*

*container structure that includes annular chamber wall structure,*

*application surface structure at one end of said annular chamber wall structure, said application surface structure defining an application surface having an array of elongated divider webs that define a corresponding array of distribution passages, said elongated divider webs having leading end surface portions of width less than said distribution passages to define flared entrance ports to said distribution passages, and*

*dispenser structure for urging said gel cosmetic product through said distribution passages to said application surface.*

*29. The dispenser of claim 28 wherein said dispenser structure includes a platform member with a circumferential wiping rib in wiping engagement with the inner surface of said annular chamber wall structure and a threaded actuator shaft in engagement with said platform member for moving said platform member towards said application surface structure for dispensing gel cosmetic product through said application surface structure.*

*30. A packaged cosmetic product comprising*

*container structure that includes annular chamber wall structure,*

*application surface structure at one end of said annular chamber wall structure, said application surface structure defining an application surface having an array of elongated divider webs that define a corresponding array of distribution passages, said elongated divider webs having tapered leading end surface portions of width less than said distribution passages to define flared entrance ports to said distribution passages,*

*gel cosmetic material of less than 200,000 centipodes viscosity in said container structure, and*

*dispenser structure for urging said gel cosmetic material through said distribution passages to said application surface.*

*31. The product of claim 30 wherein a plurality of dispensing ports are disposed at said application surface in a symmetrical array of at least fifteen ports, each said dispensing port having an effective cross-sectional area of less than about forty square millimeters in an application surface area of about twelve square centimeters.*

*32. The product of claim 31 wherein said chamber wall structure is of oval configuration, said application surface is convex and has a greater radius in the longitudinal direction than in the transverse direction, each said web has a smoothly curved leading end surface, each said distribution passage has a tapered entrance portion, and an intermediate length of uniform cross-sectional area, and each said distribution passage divider web portion has a thickness of less than two millimeters.*

*33. A packaged cosmetic product comprising*

*container structure that includes annular chamber wall structure,*

*application surface structure at one end of said annular chamber wall structure, said application surface structure defining an application surface with an array of dispensing ports directly connected to an array of distribution passages defined by an array of elongated divider webs, said elongated divider webs having tapered leading end surface portions of width less than said distribution passages to define flared entrance ports to said distribution passages,*

*gel cosmetic material of less than 200,000 centipoises viscosity in said container structure, and*

*dispenser structure for urging said gel cosmetic material through said distribution passages and said corresponding directly connected dispensing ports to said application surface.*

*34. The product of claim 33 wherein said dispensing ports are disposed at said application surface in a symmetrical array of at least fifteen ports, each said dispensing port having an effective cross-sectional area of less than about forty square millimeters in an application surface area of about twelve square centimeters.*

*35. The product of claim 33 wherein said chamber wall structure is of oval configuration, said application surface is convex and has a greater radius in the longitudinal direction than in the transverse direction, each said web has a smoothly curved leading end surface, each said distribution passage has a tapered entrance portion, and an intermediate length of uniform cross-sectional area, and each said distribution passage divider web portion has a thickness of less than two millimeters.*

*36. The product of claim 35 wherein said dispenser structure includes a platform member with a circumferential wiping rib in wiping engagement with the inner surface of said annular chamber wall structure and a threaded actuator shaft in engagement with said platform member for moving said platform member towards said application surface structure for dispensing gel cosmetic material through said application surface structure.*

* * * * *